United States Patent
Fu et al.

(10) Patent No.: US 9,242,060 B2
(45) Date of Patent: Jan. 26, 2016

(54) ELBOW FOR MASK SYSTEM

(75) Inventors: Timothy Tsun-Fai Fu, Carlingford (AU); Daniel Robert Judson, Lapstone (AU); Aaron Samuel Davidson, Newport (AU); Daniel Joseph Kaars Sijpesteijn, Seven Hills (AU); Amal Shirley Amarasinghe, West Pennant Hills (AU); Jim Saada, Kellyville (AU); Milind Chandrakant Raje, Wentworthville (AU); Sarah Dane, Bella Vista (AU)

(73) Assignee: ResMed Limited, Bella Vista (AU)

( * ) Notice: Subject to any disclaimer, the term of this patent is extended or adjusted under 35 U.S.C. 154(b) by 2545 days.

(21) Appl. No.: 11/920,652

(22) PCT Filed: May 19, 2006

(86) PCT No.: PCT/AU2006/000666
§ 371 (c)(1),
(2), (4) Date: Nov. 19, 2007

(87) PCT Pub. No.: WO2006/122369
PCT Pub. Date: Nov. 23, 2006

(65) Prior Publication Data
US 2009/0194111 A1 Aug. 6, 2009

Related U.S. Application Data

(60) Provisional application No. 60/682,827, filed on May 20, 2005, provisional application No. 60/721,967, filed on Sep. 30, 2005.

(51) Int. Cl.
*A61M 16/08* (2006.01)
*A61M 16/06* (2006.01)

(52) U.S. Cl.
CPC .............. *A61M 16/06* (2013.01); *A61M 16/08* (2013.01); *A61M 16/0816* (2013.01); *A61M 2205/42* (2013.01)

(58) Field of Classification Search
CPC .............. A61M 16/00; A61M 16/042; A61M 16/0486; A61M 16/06; A61M 16/08; A61M 16/0816; A61M 16/0875; A61M 16/20; A61M 16/201; F16L 9/18; F16L 9/19; F16L 39/00
USPC .............. 128/202.27, 204.18, 205.11, 205.19, 128/205.25, 206.27, 206.28, 207.11, 128/207.13, 912, 205.24, 206.21; 285/210, 285/292.1; 403/60, 109.4, 118, 104
See application file for complete search history.

(56) References Cited

U.S. PATENT DOCUMENTS 709,504 A * 9/1902 W. L. McGowan ....... 285/124.5
4,944,310 A 7/1990 Sullivan
(Continued)

FOREIGN PATENT DOCUMENTS

EP 1356844 10/2003
WO WO 2004/022147 3/2004
(Continued)

OTHER PUBLICATIONS
International Search Report dated Jul. 31, 2006.
(Continued)

*Primary Examiner* — Nicholas Woodall
*Assistant Examiner* — Raymond E Harris
(74) *Attorney, Agent, or Firm* — Nixon & Vanderhye P.C.

(57) ABSTRACT

An elbow for a mask system includes a proximal end adapted to be provided to the mask system, a distal end adapted to be provided to an air delivery conduit, and a baffle provided within the proximal end. The baffle has a generally planar configuration that defines an intake port that directs incoming air from the air delivery conduit into a mask cavity and an exhaust port separated from the intake port that directs exhaust air from the mask cavity to atmosphere. The baffle includes an end portion that is adapted to extend into the mask cavity defined by the mask system.

4 Claims, 10 Drawing Sheets

(56) References Cited

U.S. PATENT DOCUMENTS

| | | | |
|---|---|---|---|
| 5,918,598 | A | 7/1999 | Belfer et al. |
| 6,491,034 | B1 * | 12/2002 | Gunaratnam et al. ... 128/204.18 |
| 6,561,190 | B1 | 5/2003 | Kwok |
| 6,561,191 | B1 | 5/2003 | Kwok |
| 6,691,707 | B1 | 2/2004 | Gunaratnam et al. |
| 7,011,090 | B2 * | 3/2006 | Drew et al. ............ 128/202.27 |
| 7,290,546 | B2 | 11/2007 | Sprinkle et al. |
| 7,487,772 | B2 | 2/2009 | Ging et al. |
| 7,861,715 | B2 * | 1/2011 | Jones et al. ............ 128/204.21 |
| 2001/0032648 | A1 | 10/2001 | Jestrabek-Hart |
| 2003/0196656 | A1 * | 10/2003 | Moore et al. ............ 128/201.22 |
| 2003/0196657 | A1 * | 10/2003 | Ging et al. ............ 128/201.22 |
| 2003/0196658 | A1 * | 10/2003 | Ging et al. ............ 128/201.22 |
| 2003/0196662 | A1 * | 10/2003 | Ging et al. ............ 128/204.15 |
| 2004/0112385 | A1 | 6/2004 | Drew et al. |
| 2006/0081248 | A1 * | 4/2006 | McDonald ............ 128/205.25 |

FOREIGN PATENT DOCUMENTS

| | | |
|---|---|---|
| WO | WO 2004/096332 | 11/2004 |
| WO | WO 2006/007668 | 1/2006 |

OTHER PUBLICATIONS

Written Opinion of the International Searching Authority for PCT/AU2006/000666 mailed Jul. 31, 2006.

U.S. Appl. No. 60/590,338, filed Jul. 23, 2004.

U.S. Appl. No. 11/630,261 filed Dec. 20, 2006.

International Preliminary Report on Patentability, PCT/AU2006/000666, issued Nov. 23, 2007, 6 pgs.

Supplementary Search Report issued in European Appln. No. 06721525 (Jan. 27, 2011).

* cited by examiner

ELBOW FOR MASK SYSTEM

CROSS-REFERENCE TO APPLICATIONS

This application is the U.S. national phase of International Application No. PCT/AU2006/000666 filed 19 May 2006 which designated the U.S. and claims priority to U.S. Provisional Patent Application Nos. 60/682,827, filed May 20, 2005, and 60/721,967, filed Sep. 30, 2005, each of which is incorporated herein by reference in its entirety.

Also, PCT Application No. PCT/AU2004/000563, filed Apr. 30, 2004, and U.S. Provisional Patent Application No. 60/590,338, filed Jul. 23, 2004, are each incorporated herein by reference in its entirety.

FIELD OF THE INVENTION

The present invention relates to an elbow for use with a mask system for Non-invasive Positive Pressure Ventilation (NIPPV) and for continuous positive airway pressure (CPAP) therapy of sleep disordered breathing (SDB) conditions such as obstructive sleep apnea (OSA).

BACKGROUND OF THE INVENTION

Since the invention by Colin Sullivan of the use of nasal Continuous Positive Airway Pressure (nasal CPAP) to treat "snoring sickness" (see U.S. Pat. No. 4,944,310), there have been a number of advances directed towards improving the noise and comfort of therapy. In nasal CPAP therapy, a supply of air at positive pressure is delivered to the entrance of a patient's airways via an air delivery conduit and some form of patient interface, such as a mask. The early masks were custom made for each patient and glued on each night. A typical mask comprises: (i) a frame which defines a nose-receiving mask cavity; (ii) a seal-forming face-contacting cushion which in use is positioned between the frame and the patient's face; and (iii) a vent to atmosphere which amongst other things allows exhaled $CO_2$ to vent to atmosphere, thus reducing $CO_2$ rebreathing.

It is generally desirable for the treatment system (including the source of pressurized air and the patient interface) to be as quiet as possible so as not to disturb sleep.

The supply of air at positive pressure may be provided by a blower, sometimes referred to as a flow generator. Such devices typically include an electric motor and impeller housed in a volute. Spinning the motor (and thus the impeller) generates a flow of air. When the flow is attached to an air circuit, a pressure is created due to the impedance of the circuit. Spinning the motor faster generates a supply of air at higher pressure, but also more noise. As a fluid such as air flows through a pipe or conduit it loses pressure. Bends and curves in the pipe affect the amount of pressure loss. See Perry's Chemical Engineers Handbook 6th Edition, McGrawHill, 1984, Section 5, Fluid and Particle Mechanics. The greater the pressure drop in each component (i.e. the higher the impedance) of the air circuit (for example along the air delivery conduit) the harder the blower must work in order to provide sufficient pressure in the patient interface. The harder the blower has to work, the greater noise it will generate. Thus generally it is important to design components in the air path to have a low impedance.

A further reason for minimizing the impedance of components in the air path is to minimize pressure swings as the pressure fluctuates within the mask due to the patient breathing. A higher entry impedance at the mask will lead to a higher pressure difference between inspiration and expiration, which may lead to patient discomfort and additional cyclic noise.

The process of air venting from the mask creates noise. Since patients must wear their mask all night while sleeping, there is a need for the vent to be quiet. Some quiet vents are described in U.S. Pat. No. 6,561,190 (Kwok et al.) and U.S. Pat. No. 6,561,191 (Kwok et al.). The contents of these two patents are hereby expressly incorporated by cross-reference.

While in some mask designs—such as the ResMed MIRAGE mask—the air delivery conduit is fixed in position in relation to the frame, other masks—such as the ResMed ULTRA MIRAGE mask—include a swivel elbow. The swivel elbow enables the air delivery conduit to rotate with respect to the mask. This enables a patient to place the air delivery conduit in a preferred position such as over the head or on the left or right sides. Absent a swivel, inadvertent movement of the air delivery conduit can disrupt the seal and thus therapy.

In designing hard parts for patient interfaces, such as a mask frame and elbow constructed from polycarbonate or similar materials, regard must be had to how the part will be molded. For ease of manufacture, the tool from which a component is manufactured generally has two parts that form the shape of the component. Once the component has been formed, the tool is opened by withdrawing one part along a "line of draw" that is of constant radius (including a straight line). Parts must be designed within the constraints of what is manufacturable.

Some swivel elbows, such as the one used in ResMed's ULTRA MIRAGE mask, incorporate a vent. See U.S. Pat. No. 6,691,707 (Gunaratnam et al.). Incorporating a vent in a swivel elbow can allow the patient some control over the direction in which air is vented. Thus the vented air may be directed away from the patient or anyone sleeping close by. Incorporation of a vent in an elbow can simplify molding of the mask frame.

Vent flow rate, and hence vent $CO_2$ flow rate is a function of the pressure differential between the mask interior and ambient pressure. The higher the differential, the higher the flow rate. With a fixed vent, whether adequate $CO_2$ washout occurs is defined by what happens at the lowest operating mask pressure, typically 4 $cmH_2O$. The flow rate is also a function of vent geometry.

In some prior art vents incorporated in elbows, air entering the elbow from a blower can short-circuit the mask and pass straight out the vent.

Another known swivel elbow which includes a vent is described in International Patent Application PCT/AU2003/001162 (published as WO 2004/022147) to Drew et al., the contents of which are hereby expressly incorporated by cross-reference. This elbow includes a baffle in the elbow as described in the '1162 PCT application. A commercial version of this elbow is found in ResMed's ACTIVA mask system.

A potential problem with including a baffle in the elbow is that while it may assist with $CO_2$ washout, it may impede flow from the blower. Increased impedance from a baffle may require a blower to work harder to generate enough pressure and thus result in increased noise. A poorly designed baffle and corresponding vent may be unnecessarily noisy. A possible way of avoiding increased impedance is to make the elbow larger overall, however this is undesirable for other reasons such as aesthetics.

SUMMARY OF THE INVENTION

One aspect of the invention relates to an elbow including a baffle that defines separate conduit and vent pathways for conducting respective airflow streams in use so that they do not interfere with one another.

Another aspect of the invention relates to an elbow for a mask system. The elbow includes a proximal end adapted to be provided to the mask system, a distal end adapted to be provided to an air delivery conduit, and a baffle provided within the proximal end. The baffle has a generally planar configuration that defines an intake port that directs incoming air from the air delivery conduit into a mask cavity and an exhaust port separated from the intake port that directs exhaust air from the mask cavity to atmosphere. The baffle includes an end portion that is adapted to extend into the mask cavity defined by the mask system.

Yet another aspect of the invention relates to an elbow for a mask system. The elbow includes a proximal end adapted to be provided to the mask system, a distal end adapted to be provided to an air delivery conduit, and a release mechanism provided to the proximal end. The release mechanism includes diametrically opposed tongues adapted to releasably engage with the mask system. Each tongue includes at least one of a reinforcement lug extending from an exterior surface and an internal rib extending from an internal surface to provide additional strength to each tongue.

Still another aspect of the invention relates to an elbow for a mask system. The elbow includes a proximal end adapted to be provided to the mask system and a distal end adapted to be provided to an air delivery conduit. The proximal end includes a generally cylindrical portion and a baffle provided within the cylindrical portion. The baffle defines an intake port that directs incoming air from the air delivery conduit into a mask cavity and an exhaust port separated from the intake port that directs exhaust air from the mask cavity to atmosphere. The baffle includes an end portion that protrudes beyond the cylindrical portion. The end portion has an arcuate configuration in plan view such that a curvature of the end portion begins and ends at intersection points at which the end portion protrudes beyond the cylindrical portion.

Still another aspect of the invention relates to an elbow assembly for a mask system. The elbow assembly includes an elbow and a vent cover. The elbow includes a proximal end adapted to be provided to the mask system, a distal end adapted to be provided to an air delivery conduit, and a baffle provided within the proximal end. The baffle defines an intake port that directs incoming air from the air delivery conduit into a mask cavity and an exhaust port separated from the intake port that directs exhaust air from the mask cavity to atmosphere. The baffle includes an end portion that is adapted to extend into the mask cavity defined by the mask system. The vent cover is connected to the elbow at an outlet of the exhaust port with a snap-fit. The vent cover includes at least one vent aperture for gas washout. The vent cover is non-removable from the elbow when connected.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

1. Mask System

Figure 1:
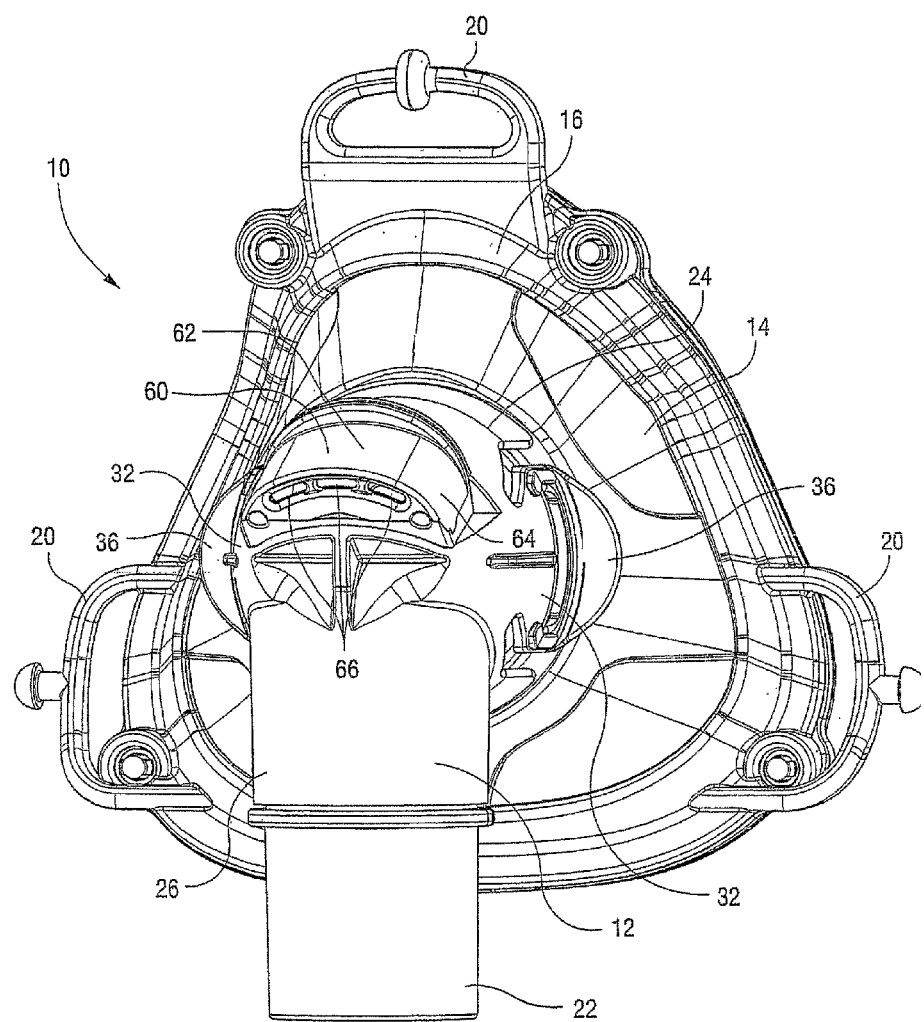
FIG. 1 is a front perspective view of a mask system including an elbow constructed according to an embodiment of the present invention.
Figure 2:
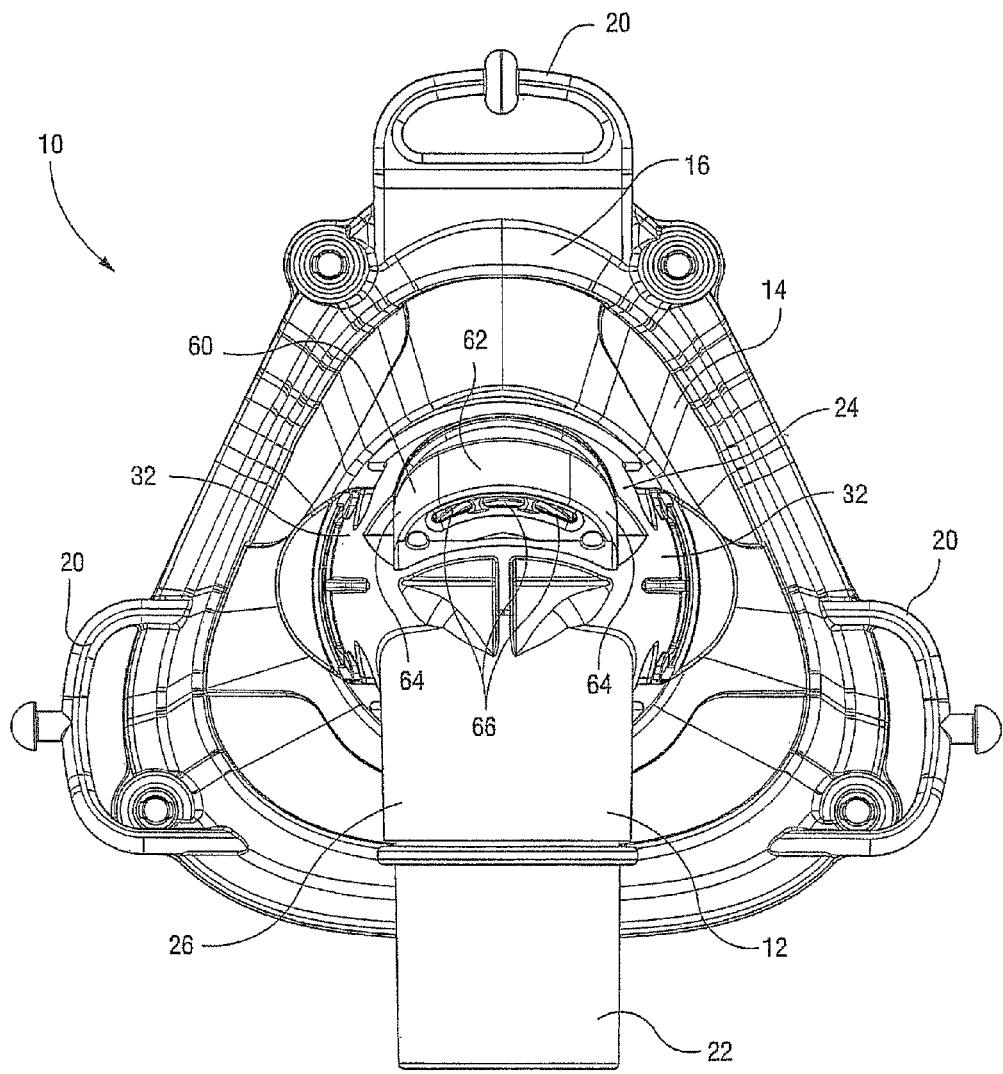
FIG. 2 is a front view of the mask system shown in FIG. 1.
Figure 3:
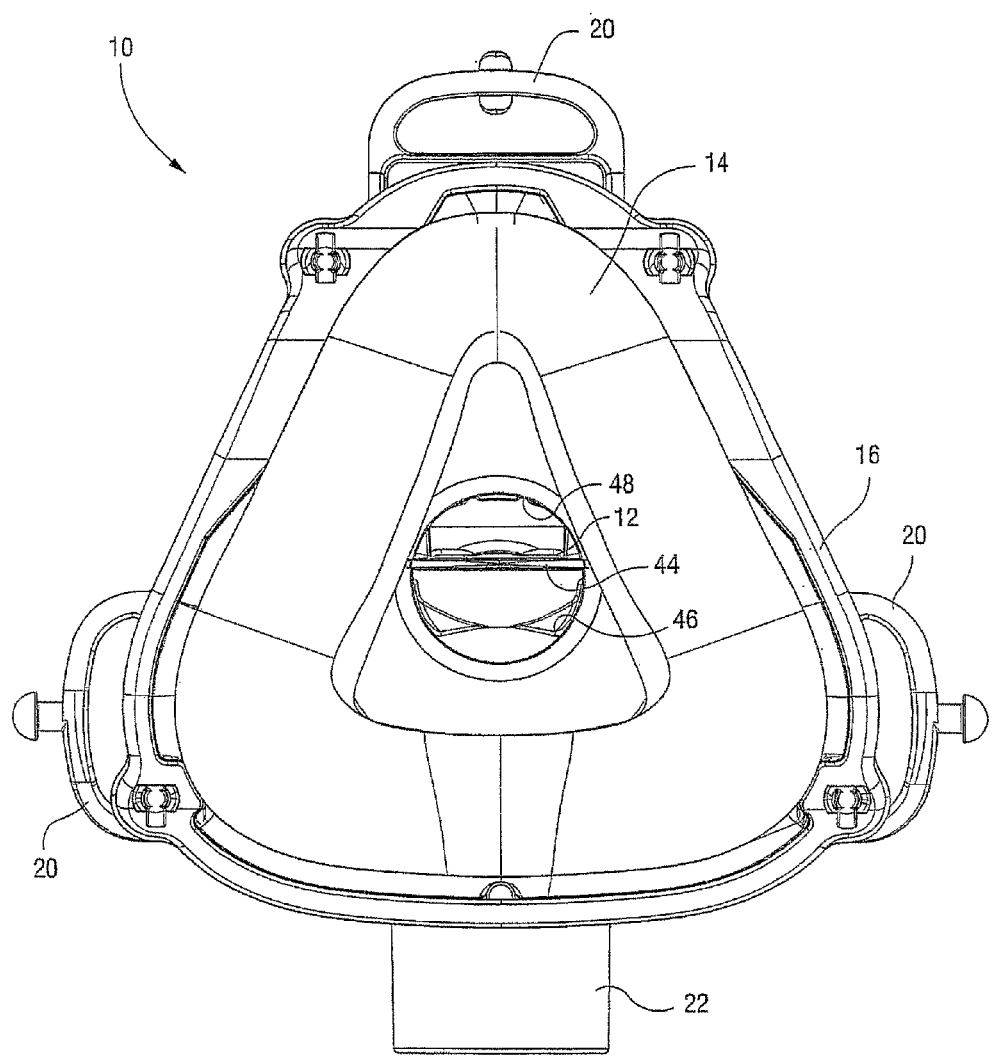
FIG. 3 is a rear view of the mask system shown in FIG. 1.
Figure 4:
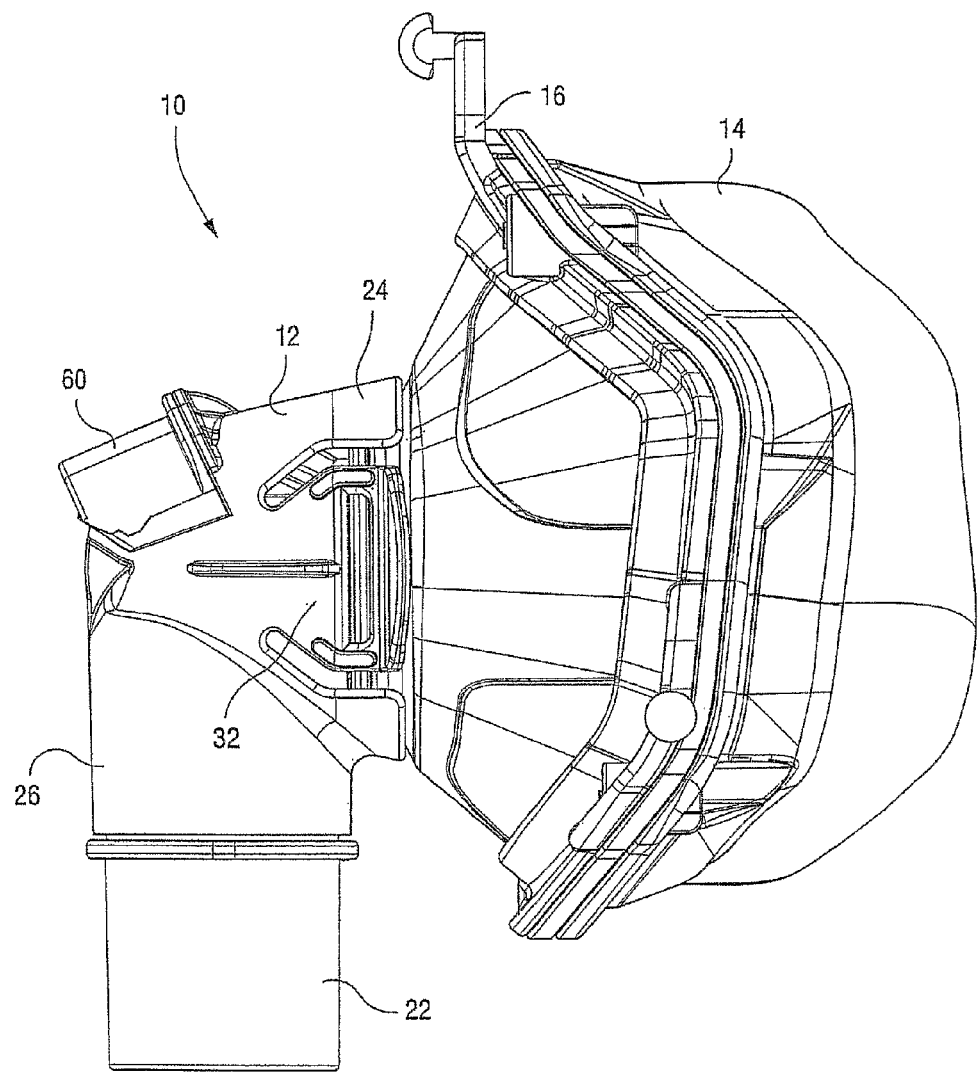
FIG. 4 is a side view of the mask system shown in FIG. 1.
Figure 5:
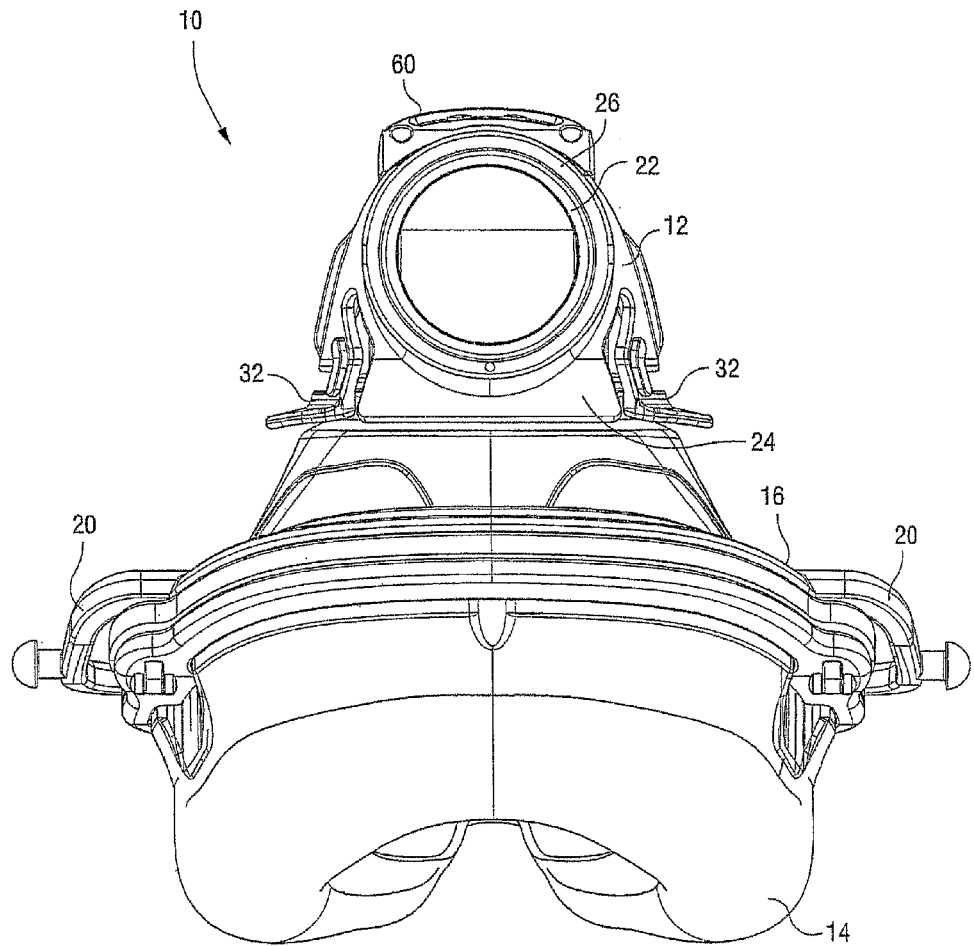
FIG. 5 is a bottom view of the mask system shown in FIG. 1.

FIGS. 1-7 illustrate a mask system 10 including an elbow 12 constructed according to an embodiment of the present invention. As illustrated, the mask system 10 includes a shell/cushion 14 adapted to form a seal with the patient's face, a frame 16 that is provided, e.g., mounted, to the shell/cushion 14, a retaining ring 18 (see FIG. 6) that is received within a front aperture provided in the shell/cushion 14, and the elbow 12 which is adapted to engage with the shell/cushion 14 and the retaining ring 18. A headgear assembly (not shown) may be removably attached to the frame 16, e.g., via anchor points 20, to maintain the frame 16 and the shell/cushion 14 in a desired adjusted position on the patient's face. In the illustrated embodiment, the elbow 12 includes a swivel 22 structured to be connected to an air delivery tube that delivers breathable gas to the patient.

Further details and embodiments of the shell/cushion 14, the frame 16, and the retaining ring 18 of the mask system 10 are disclosed in PCT Application No. PCT/AU2004/000563, filed Apr. 30, 2004, the entirety incorporated herein by reference. While the elbow 12 is described as being implemented into a mask system 10 of the type described above, it may be implemented into other mask systems. That is, the mask system 10 is merely exemplary, and aspects of the present invention may be incorporated into any suitable mask system, e.g., full-face mask, mouth mask, or a nasal mask.

2. Elbow

Figure 6:
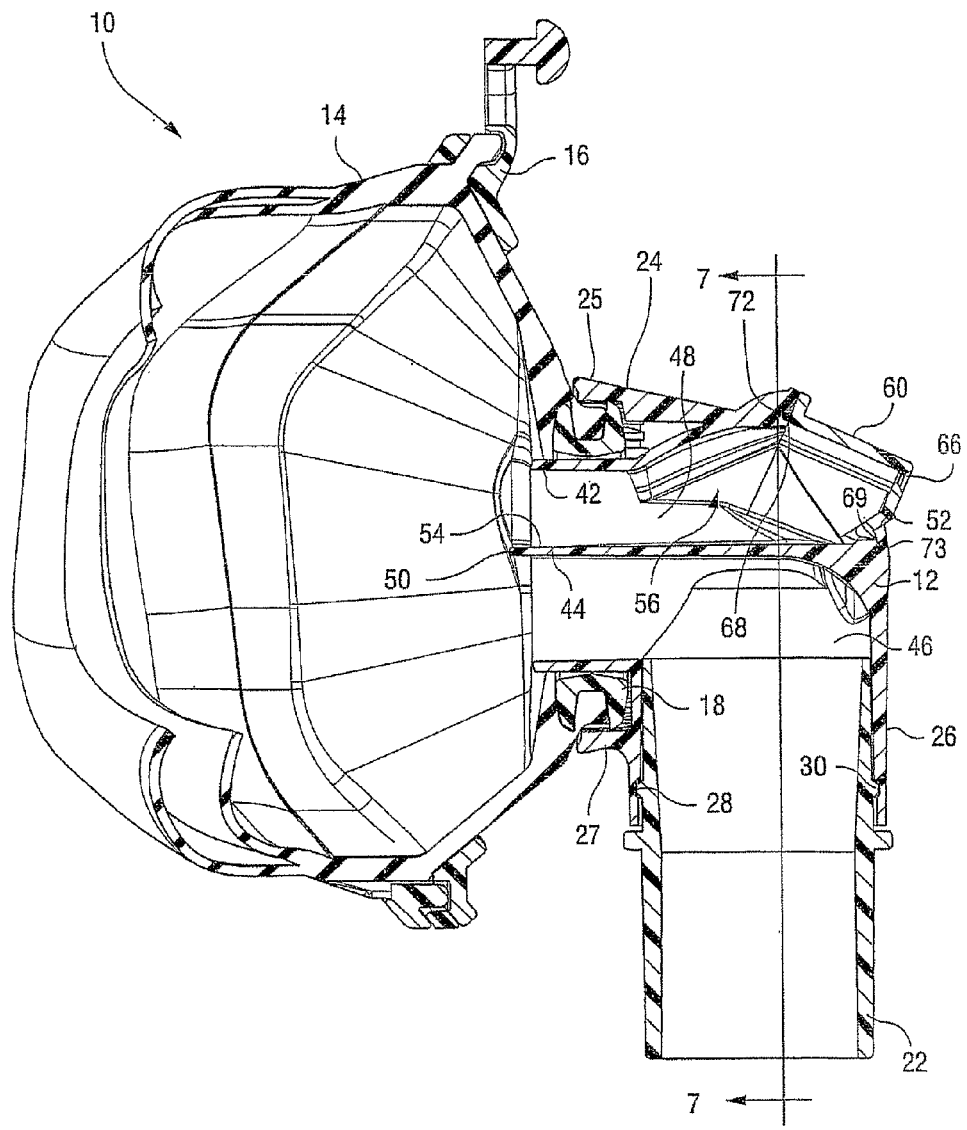
FIG. 6 is a cross-sectional view of the mask system shown in FIG. 1.
Figure 7:
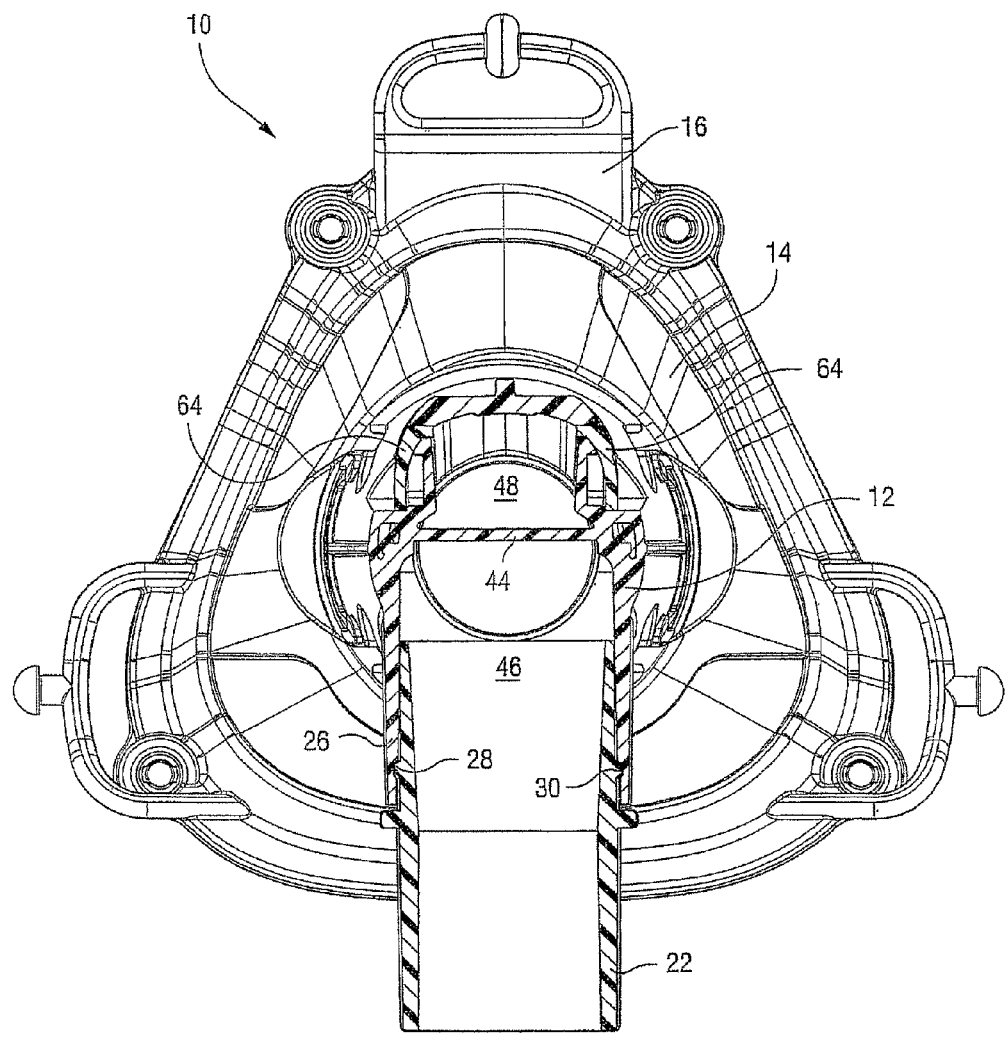
FIG. 7 is a cross-sectional view through line 7-7 of FIG. 6.
Figure 8:
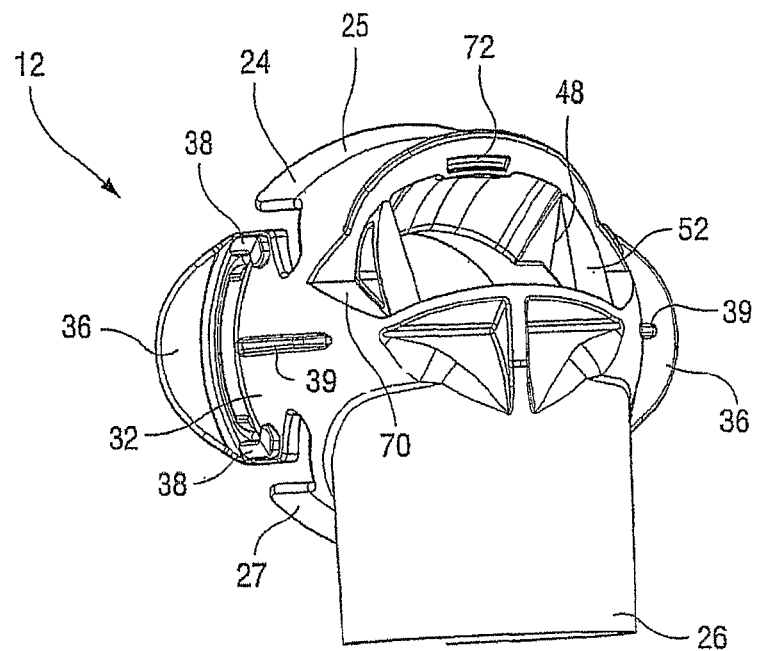
FIG. 8 is a front perspective view of the elbow shown in FIG. 1 removed from the mask system and with the vent cover and swivel removed from the elbow.
Figure 9:
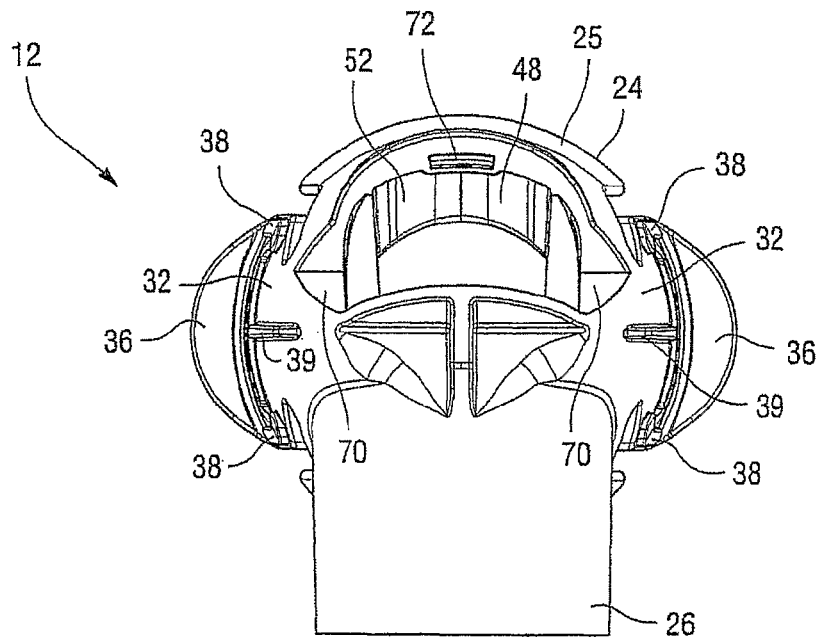
FIG. 9 is a front view of the elbow shown in FIG. 8.

As illustrated in FIGS. 1-7, the elbow 12 is generally L-shaped and includes a proximal end 24 adapted to engage with the shell/cushion 14 and the retaining ring 18, and a distal end 26 adapted to be connected to an air delivery tube. In the illustrated embodiment, the distal end 26 is rotatably connected to the air delivery tube via a swivel 22. As best shown in FIGS. 6 and 7, the distal end 26 is generally cylindrical and includes an annular groove 28 on an inwardly facing surface. The swivel 22 includes an annular lip 30 on an outwardly facing surface that engages within the annular groove 28 of the elbow 12 to allow selective attachment to and detachment from the elbow 12. The swivel is optional and the elbow 12 may be directly connected to the air delivery tube.

Figure 10:
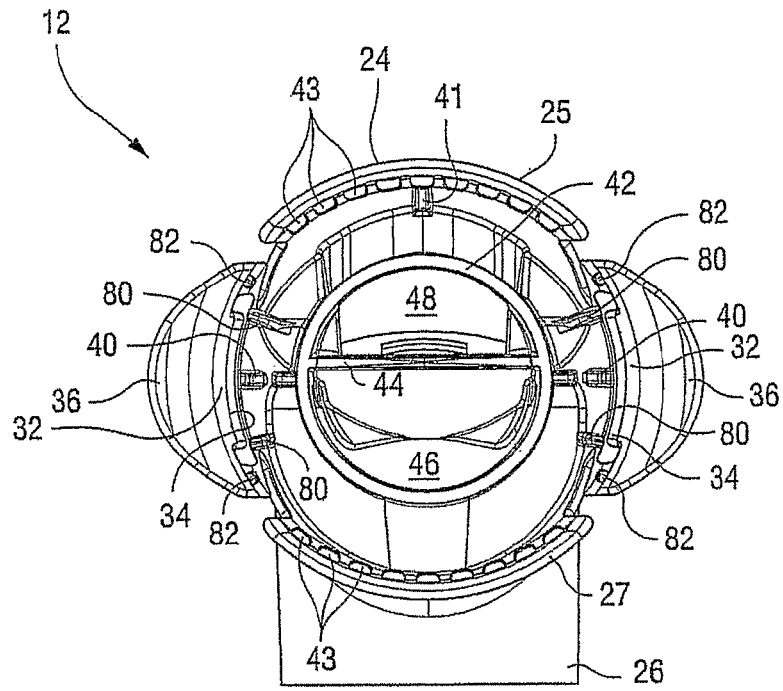
FIG. 10 is a rear view of the elbow shown in FIG. 8.
Figure 11:
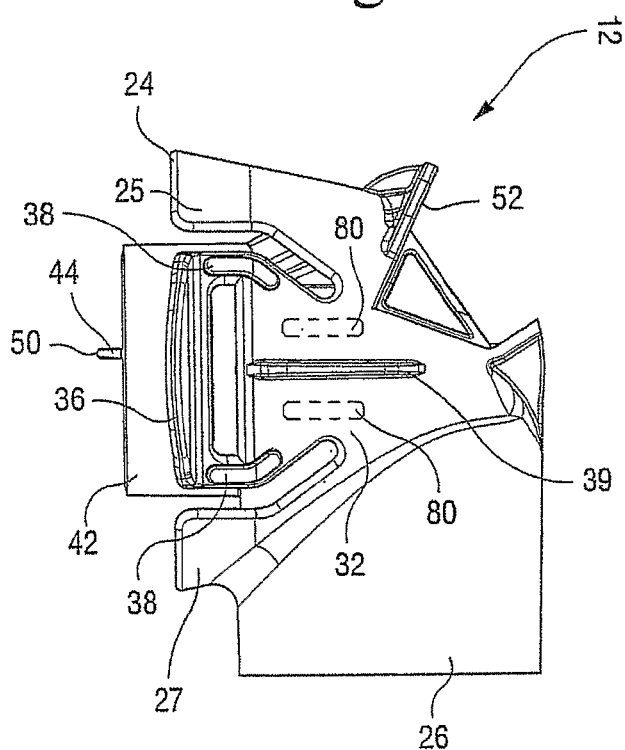
FIG. 11 is a side view of the elbow shown in FIG. 8.
Figure 12:
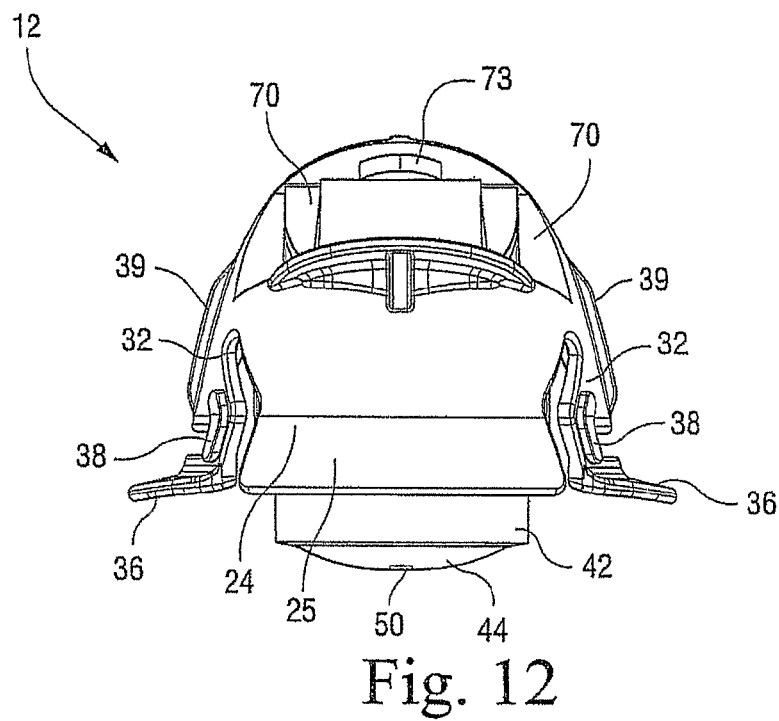
FIG. 12 is a top view of the elbow shown in FIG. 8.
Figure 13:
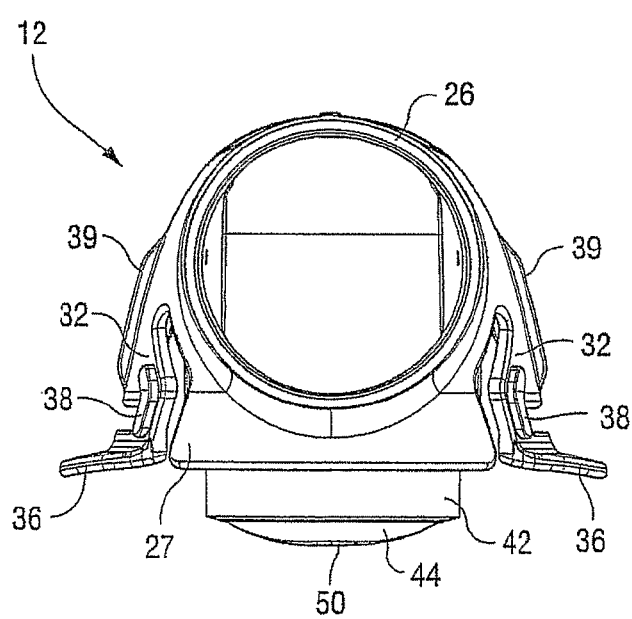
FIG. 13 is a bottom view of the elbow shown in FIG. 8.

FIGS. 8-13 show the elbow 12 in greater detail. As illustrated, the proximal end 24 provides a release mechanism including two diametrically opposed tongues 32. Each tongue 32 includes an arcuate undercut 34 (see FIG. 10) on an inwardly facing surface that is adapted to releasably engage with the retaining ring 18. Also, finger grips 36 (as best shown in FIGS. 10, 12, and 13) are provided on the ends of the tongues 32 to enable a user to pull the tongues 32 radially outwardly to disassemble the elbow 12 from the mask system 10, e.g., for cleaning. As illustrated, the finger grips 36 protrude outwardly from respective tongues 32 to make the finger grips 36 easier to grab, especially for patients with relatively large fingers. This arrangement of the finger grips 36 facilitates removal of the elbow 12. In an embodiment, each finger grip is 4-10 mm deep, preferably 6 mm deep. The elbow 12 may be sized so as to freely rotate with respect to the shell/cushion 14 and retaining ring 18. Further details of the releasable elbow connection are provided in PCT Application No. PCT/AU2004/000563 incorporated herein by reference Also, each tongue 32 includes reinforcement lugs 38 and a central rib 39 (see FIGS. 8, 9, and 11-13) extending from an exterior surface. As illustrated the reinforcement lugs 38 are provided on opposing ends of each tongue 32 and the central rib 39 is provided on a central portion of each tongue 32 between the lugs 38. In the illustrated embodiment, as viewed in FIG. 11, each lug 38 has a general v-shape and the rib 39 has a general linear shape. However, other shapes and configurations are possible. Further, each tongue 32 includes an internal rib 40 (see FIG. 10) extending from an internal surface. The lugs 38, rib 39, and rib 40 on each tongue 32 provide additional strength and stiffness to each tongue 32 to prevent cracking or fatiguing of the elbow 12 during assembly and disassembly processes. The additional stiffness also resists accidental elbow disassembly.

In addition, each tongue 32 includes upper and lower internal ribs 80 extending from an internal surface (see FIG. 10 and dashed lines in FIG. 11). The internal ribs 80 are provided at the point the tongues 32 flex in use, and provide stress relief.

Further, each tongue 32 includes bridges 82 extending from an internal surface (see FIG. 10). As illustrated, the bridges 82 are provided on opposing ends of each tongue 32. In use, the bridges 82 apply a pre-load and bear on the outside of the retaining ring 18 when the elbow 12 is engaged with the shell/cushion 14 and the retaining ring 18. This arrangement helps to prevent accidental disassembly and reduces rotational friction. In addition, the bridges 82 prevent the tongues 32 from stopping on the shell/cushion 14.

As best shown in FIG. 10, the top wall 25 of the elbow 12 includes an internal rib 41 extending from an internal surface. The internal rib 41 prevents the retaining ring 18 from pivoting when the elbow 12 is engaged with the shell/cushion 14 and the retaining ring 18. This arrangement prevents elbow disassembly.

Also, as best shown in FIG. 10, the top and bottom walls 25, 27 each include castellations or a series of protrusions 43 extending from an internal surface. The series of protrusions 43 change the effective diameter defined between the top and bottom walls 25, 27, thereby reducing the gap between the top and bottom walls 25, 27 and the shell/cushion 14 when the elbow 12 is engaged with the shell/cushion 14 and the retaining ring 18 (see FIG. 6). The series of protrusions 43 may also help to grip the silicon material of the shell/cushion 14. This arrangement minimizes accidental elbow disassembly. In the illustrated embodiment, each of the protrusions 43 has a rounded, hump-like shape. However, the protrusions 43 may have other suitable shapes, e.g., square-like. It is noted that sharper corner edges of each protrusion 43 may facilitate gripping of the silicon material of the shell/cushion 14 in use. Also, the series of protrusions 43 adds thickness to the upper and lower walls 25, 27 in a manner that facilitates molding of the elbow 12. In another embodiment, no castellations may be provided, but rather a single uninterrupted surface of the same diameter of the castellations.

As best shown in FIGS. 6, 7, 8, and 10, the proximal end 24 includes a generally cylindrical portion 42 and a baffle 44 provided within the cylindrical portion 42 that defines two fluid pathways. Specifically, the baffle 44 defines an intake port or conduit pathway 46 that allows flow between the air delivery tube and the mask cavity. The baffle 44 also defines an exhaust port or vent pathway 48 that allows flow between the mask cavity and atmosphere. In the illustrated embodiment, the baffle 44 has a generally planar configuration. However, the baffle 44 may have a curved configuration or any other suitable configuration for separating the exhaust port 48 from the intake port 46. For example, U.S. Provisional Patent Application No. 60/590,338, filed Jul. 23, 2004, the entirety incorporated herein by reference, discloses an elbow with a curved baffle.

As best shown in FIG. 6, the baffle 44 includes an end portion 50 that extends beyond the cylindrical portion 42 and tongues 32. When the elbow 12 is mounted to the mask system 10, the baffle 44 extends into the mask cavity to reduce noise and improve $CO_2$ washout. With respect to the baffle disclosed in U.S. Provisional Patent Application No. 60/590, 338, the baffle 44 protrudes deeper into the mask cavity to ensure a greater divide between inlet air and exhaust air. For example, the baffle 44 may extend more than approximately 1.8 mm into the mask cavity, e.g., in a range of about 1.8-2.5 nm. This arrangement helps to encourage the fresh inlet air arriving at the mask cavity from the air delivery tube to continue into the mask cavity for inhalation. The exhaust air can then flow along the top of the baffle 44 towards the exhaust outlet 52 Thus, the incoming and outgoing airstreams do not interfere with one another.

The end portion 50 of the baffle 44 has a radius or arcuate configuration in plan view (e.g., see FIGS. 12 and 13) in order to avoid any sharp edges that may contact the patient's face, e.g., nose. Specifically, as shown in FIGS. 12 and 13, the end portion 50 protrudes beyond the cylindrical portion 42. Moreover, the curvature of the end portion 50 begins and ends at the intersection points at which the end portion 50 protrudes past the cylindrical portion 42.

As best shown in FIG. 6, the exhaust port 48 generally tapers or expands from a narrower inlet 54 positioned adjacent the mask cavity to a wider outlet 52 positioned adjacent the atmosphere. That is, the exhaust port 48 is initially narrow as exhaust air flows past the baffle 44, which expands into a chamber 56 before the air exhausts to atmosphere. This expansion chamber 56 helps to reduce turbulence and air velocity, and leads to a reduction in overall and cyclic noise.

The elbow 12 may be molded from any suitable material, e.g., polypropylene or polycarbonate.

3. Vent Cover

As best shown in FIGS. 1, 2, 4, and 6, a vent cover 60 is connected to the elbow 12 with a snap-fit, for example. The vent cover 60 is constructed from polypropylene or another material suitable for snap-fits. In use, the vent cover 60 is structured to direct exhaust air from the mask system 10 in manner that minimizes noise and avoids disturbance of a bed partner.

The vent cover 60 includes a cap portion 62 and leg portions 64 on opposing sides of the cap portion 62. The front face of the cap portion 62 includes at least one vent aperture 66, e.g., three vent apertures, extending from an interior of the cap portion 62 to an exterior of the cap portion 62 for gas washout. In the illustrated embodiment, the vent apertures have an oval configuration. However, the vent apertures 66 may have any other suitable configuration as is known in the art.

The rear portion of the vent cover 60 includes a first retaining tab 68 and the front portion of the vent cover 60 includes a second retaining tab 69 (see FIG. 6). The first and second retaining tabs 68, 69 are structured to retain the vent cover 60 on the elbow 12. Specifically, as shown in FIGS. 6, 8, 9, and 12, the elbow 12 includes recessed portions 70 and upper and lower slots 72, 73 adjacent the exhaust outlet 52. The recessed portions 70 and slots 72, 73 are integrally molded into the elbow 12. The vent cover 60 is connected to the elbow 12 by placing the leg portions 64 into respective recessed portions 70 and then engaging the first and second retaining tabs 68, 69 within respective slots 72, 73 with a snap-fit (see FIG. 6). This interlocks the vent cover 60 with the elbow 12.

Moreover, the vent cover 60 is positioned in covering relation with respect to the exhaust outlet 52 and the vent apertures 66 are configured to direct exhaust gas along the direction of the air delivery tube. This arrangement helps to prevent exhaust air from contacting the bed partner or bed sheets and thus reducing irritation and noise. The vent cover 60 is not molded in one piece along with the elbow 12 due to the direction of the vent apertures 66.

As noted above, the vent cover 60 is a separate component which is snapped onto the elbow 12 during the assembly process. In the illustrated embodiment, the vent cover 60 is not removable once it is snapped into place. Specifically, the configuration and position of the retaining tabs 68, 69 and respective slots 72, 73 prevents removal of the vent cover 60. Also, no leverage features, e.g., protrusions or finger grips, are provided on the vent cover 60 in order to make it difficult for one to force the vent cover from the elbow 12.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

The invention claimed is:

1. An elbow for use with a mask assembly, comprising:
   a proximal end adapted to be provided to the mask assembly;
   a distal end adapted to be provided to an air delivery conduit,
   the proximal end including a generally cylindrical portion and a baffle provided within the cylindrical portion, the baffle defining an intake port configured to direct incoming air from the air delivery conduit into a mask cavity of the mask assembly and an exhaust port separated from the intake port and configured to direct exhaust air from the mask cavity to atmosphere,
   wherein the baffle includes an end portion that protrudes beyond the cylindrical portion, and the end portion having an arcuate configuration in plan view such that a curvature of the end portion begins and ends at intersection points at which the end portion protrudes beyond the cylindrical portion.

2. The elbow according to claim 1, wherein the end portion is adapted to extend into the mask cavity which is defined by the mask assembly.

3. The elbow according to claim 1, wherein the baffle has a generally planar configuration.

4. The elbow according to claim 1, wherein the end portion has an arcuate configuration in plan view to avoid sharp edges that may contact a patient's face.

* * * * *